United States Patent [19]

Stefaniak et al.

[11] Patent Number: 5,004,124

[45] Date of Patent: Apr. 2, 1991

[54] METHOD AND APPARATUS FOR DISPENSING A FLUID SUBSTANCE

[75] Inventors: Philip S. Stefaniak, Hanover Park, Ill.; Daniel H. Fine, Leonia, N.J.

[73] Assignee: The Trustees of Columbia in The City of New York, New York, N.Y.

[21] Appl. No.: 281,494

[22] Filed: Dec. 8, 1988

[51] Int. Cl.[5] .............................................. B67D 5/52
[52] U.S. Cl. ................................... 222/136; 222/137; 222/391; 222/324; 222/326; 222/327; 433/90; 604/224; 604/228
[58] Field of Search ..................... 433/89, 90; 222/136, 222/137, 390, 391, 323, 327, 326, 146.5, 386; 401/176, 181; 226/160, 164, 167; 228/52, 53, 41; 604/224, 228, 233

[56] References Cited

U.S. PATENT DOCUMENTS

| | | | |
|---|---|---|---|
| 1,709,691 | 4/1929 | Steuer | 604/233 |
| 2,303,947 | 12/1942 | Moore | 226/167 |
| 2,731,176 | 1/1956 | Crewe | 222/391 |
| 3,221,409 | 12/1965 | Thiel et al. | 222/391 |
| 3,977,574 | 8/1976 | Thomas | 604/224 |
| 4,364,388 | 12/1982 | Cech | 604/224 |
| 4,444,560 | 4/1984 | Jacklich | 222/391 |
| 4,566,610 | 1/1986 | Herb | 222/391 |
| 4,641,766 | 2/1987 | Vlasich | 222/391 |
| 4,693,684 | 9/1987 | Blatherwick et al. | 433/90 |
| 4,826,053 | 5/1989 | Keller | 222/326 |

*Primary Examiner*—H. Grant Skaggs
*Attorney, Agent, or Firm*—John P. White

[57] ABSTRACT

A method and apparatus for controllably dispensing a fluid substance on a repetitive, variable basis utilize a piston-cylinder type handheld finger operated dispenser. The dispenser includes a generally cylindrical body for containing a supply of the fluid substance to be dispensed, a formed tip through which the fluid substance may be dispensed, a piston and a piston rod for use in dispensing the fluid substance from the cylinder and a formed gouge or actuator for initiating movement of the piston rod to dispense the fluid substance in amounts controlled by the skill and desire of the user. The actuator is formed from a harder material than the material used to form the piston rod so that gouges or teeth are formed by the actuator during usage along the length of the piston rod, the spacing between adjacent teeth being variably selected by the user. A specific application of the dispenser is for use in dispensing topical dental medicine by a user in his own oral cavity.

65 Claims, 7 Drawing Sheets

METHOD AND APPARATUS FOR DISPENSING A FLUID SUBSTANCE

BACKGROUND OF THE INVENTION

A. Field of the Invention

The present invention generally relates to fluid dispensers, and, more particularly, to a new and improved method and apparatus for dispensing a non-compressible fluid substance, for example, a topical dental preventative medicine, in variable amounts by means of a handheld, finger operated, piston-cylinder type dispenser.

B. Description of the Prior Art

Currently periodontal disease affects approximately three out of four adults in the United States over the age of thirty-five years and is responsible for at least seventy percent of all tooth loss in adults. Typically, the disease progresses from an early, reversible stage, known as gingivitis, to a later, irreversible stage, known as periodontitis, in which both teeth and bone are destroyed. Common treatment for periodontal disease involves removing the bacterial colonies by scraping or surgery, operations performed by licensed periodontal dentists. A person can reduce his chances of experiencing periodontal disease by proper tooth care, including regular brushing and flossing, and by periodic dental visits.

More recently, researchers have been investigating topical dental preventative treatment medicine. For example, the oral compositions disclosed in U.S. Pat. No. 4,515,771 when topically applied to the gumline on a regular basis effectively eliminates the bacteria associated with gingivitis. Such treatments typically have been applied in clinical studies by dentists using professional applicators.

The periodic and timely application of a topical periodontal medicine can save a person much pain and expense. However, daily visits to a dentist are impractical for the contemplated widespread use of the oral compositions disclosed in the above-mentioned '771 patent. Therefore, a need exists for a simple, inexpensive applicator that a person can use at home on a frequent basis.

Applicators for dispensing non-compressible fluid substances, for example, topical dental medicines of the type disclosed in the '771 patent, are old and well known in the prior art as exemplified by not only the dispenser disclosed in the '771 patent and described therein as being capable of being used by either a professional or the patient himself, but also in the following U.S. Pat. Nos. 1,410,530; 2,086,462; 2,505,028; 2,752,920; 2,847,009; 2,875,761; 3,051,172; 3,161,323; 3,164,303; 3,220,413; 3,581,399; 3,900,954; 4,295,828; 4,330,280; 4,391,590 and 4,641,766. Most of the prior art applicators disclosed in the above patents are relatively complex and expensive and are awkward and generally not suitable for use by a patient on himself because, generally, they were designed to be used by one person on another person.

For example, the device disclosed in the '530 patent is a pump for use in evacuating blood from body cavities during surgery. The '462 patent discloses a dental instrument for discharging wax or other material that utilizes a rack or indexing rod having a plurality of preformed, spaced apart teeth and a pivotal pawl for advancing the rod along an elongate axis to dispense on a repetitive basis a predetermined amount of wax, the amount being determined by the spacing between adjacent preformed teeth.

The '028 patent, the '920 patent, the '009 patent, the '761 patent, the '303 patent, the '413 patent, the '399 patent and the '954 patent all disclose piston-cylinder type dispensers for dispensing non-compressible fluid substances having in-line piston rods or plungers disposed for movement along the central axes of the cylinders. The force used to dispense the fluid substances from the devices disclosed in these patents is applied by a hand or finger to the end of the piston rods or plungers. These prior art devices, while suitable for some purposes, are difficult for a generally unskilled person to use on himself, particularly in applying a topical dental medicine on his own gums.

The '828 patent, the '280 patent and the '590 patent all disclose piston-cylinder type dispensing apparatus used in conjunction with two-piece, manually engageable handles for applying force to the ends of and generally along the longitudinal axes of the piston rods of the apparatus. Again, these prior art devices are awkward to use for certain purposes, for example, in applying topical dental medicine to one's own jaws.

The '172 patent and the '323 patent disclose piston-cylinder type fluid substance dispensers having similar, somewhat complex mechanical systems for applying force to dispense the fluid substances. Specifically, the dispensers of these patents utilize elongated index rods or racks with a plurality of preformed, spaced apart teeth and pivotally mounted pawls for advancing the piston rods in predetermined, precise steps, thereby dispensing the same amount of the fluid substances on a repetitive basis. In addition to being mechanically complex, the devices of these patents are not readily adapted to be used by a person in dispensing a fluid substance, for example, a topical dental medicine, on himself.

The '771 patent, discussed above, discloses a somewhat complex, electrically driven dispensing device for use by a patient or a professional in applying the topical dental preventative medicine disposed therein to the gums of a patient. In addition to requiring a supply of batteries to power the dispenser, it is believed that the configuration of the dispensing apparatus may not be the most efficient for use by a patient in dispensing a topical dental medicine on his own gums.

The '766 patent also discloses a piston-cylinder type dispensing apparatus utilizing a piston rod having a plurality of preformed, equally spaced teeth disposed along its length. The preformed teeth on the piston rod cooperate with a pair of actuating arms pivotally secured to the cylinder body to dispense on a repetitive basis the same amount of a fluid substance.

While suitable for some purposes, all of the above prior art dispensers have one or more drawbacks that render them unsuitable for other purposes. More specifically, a need exists for an economical, simple, easy to use dispenser for use by a patient in applying topical dental medicine to himself at a rate controlled by the skill and desire of the patient.

SUMMARY OF THE INVENTION

An object of the present invention is to provide a new and improved method and apparatus for controllably dispensing a fluid substance on a repetitive basis from a piston-cylinder dispenser in desired amounts.

Another object of the present invention is to provide a new and improved method and apparatus for use by a person in controllably dispensing a topical dental medicine on himself at a rate determined by his own skill and desire.

Another object of the present invention is to provide a new and improved method and apparatus for controllably dispensing a fluid substance from a piston-cylinder dispenser at a rate controlled by the person operating the dispenser.

Briefly, the present invention is directed to a new and improved method and apparatus for controllably dispensing a fluid substance on a repetitive, variable basis from a piston-cylinder type dispenser. The method and apparatus of the present invention have particular application in the dispensing of topical dental medicine by a patient in his own oral cavity through a handheld, finger operated dispenser that is inexpensive and easy to operate. A dispenser constructed in accordance with the principles of the present invention also has general application in dispensing any one of a number of different fluid substances.

The inventive dispenser includes a generally cylindrical body for containing a supply of the fluid substance to be dispensed, a formed tip through which the fluid substance may be dispensed, a piston and a piston rod for use in dispensing the fluid substance from the cylinder and a formed gouge or actuator for initiating movement of the piston rod to dispense the fluid substance in amounts controlled by the skill and desire of the user. Importantly, the actuator is formed from a harder material than the material used to form the piston rod so that gouges or teeth are formed during actual usage by the actuator along the length of the piston rod, the spacing between adjacent teeth being selected by the user. In this manner, the dispenser is capable of dispensing variable amounts of the fluid substance during successive operations.

BRIEF DESCRIPTION OF THE DRAWING

The above and other objects, advantages and novel features of the present invention will become apparent from the following detailed description of a preferred embodiment of the present invention illustrated in the accompanying drawing wherein.

DESCRIPTION OF THE PREFERRED EMBODIMENT

Referring to the drawing and initially to FIGS. 1-6, there is illustrated a new and improved dispenser 20, constructed in accordance with the principles of the present invention, for controllably dispensing a fluid substance. The dispenser 20 is particularly adapted for use by a patient in dispensing an extruded bead of topical dental preventative medicine to selected sites within his own oral cavity, for example, his own jaws, by means of the handheld, finger operated dispenser 20. Preferably, a specific topical dental preventative medicine for use with the dispenser 20 is formulated in accordance with the oral compositions for the preventative treatment of dental disease disclosed in the above-identified U.S. Pat. No. 4,515,771, the disclosure of which is incorporated herein by reference for all purposes.

The dispenser 20 includes an elongate, generally cylindrical body 22 in which a fluid substance, such as a topical dental preventative medicine, to be dispensed by the dispenser 20 is disposed. In addition, the dispenser 20 includes an elongate piston rod 24 having a generally "X-shaped", transverse crosssection (FIG. 6), an enlarged piston 26 disposed at one longitudinal end of the piston rod 24 and an enlarged planar section or flange 28 disposed at the opposite longitudinal end of the piston rod 24. Preferably, the outer diameter of the piston 26 is substantially equal to the inner diameter of the cylindrical body 22, thereby enabling a sliding, interference fit therebetween to achieve the dispensing or extruding of a bead of the fluid substance contained within the cylinder 22. Similarly, the outer diameter of the flange 28 is approximately equal to the inner diameter of a generally cylindrical actuator handle 30 to prevent substantial transverse shifting or lateral movement of the piston rod 24 within the body 22 and the actuator handle 30.

Figure 4:
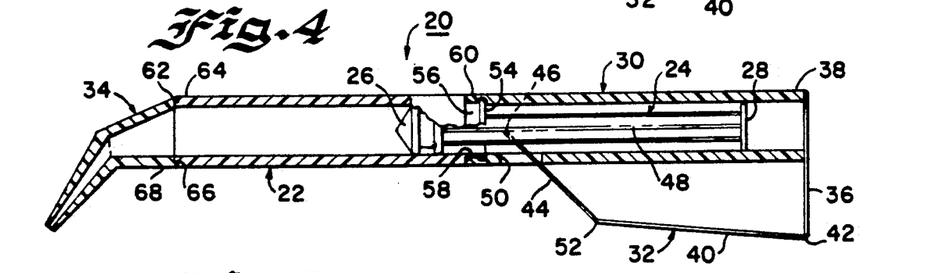
FIG. 4 is a cross-sectional view of the dispenser of FIG. 1 depicting the actuator in engagement with the piston rod of the dispenser.
Figure 5:
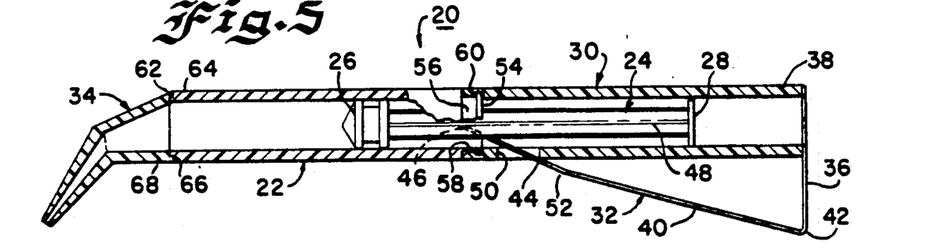
FIG. 5 is a cross-sectional view of the dispenser of FIG. 1 depicting the actuator fully extended in engagement with the piston rod of the dispenser.

In accordance with an important feature of the present invention, a formed, metal gouge or actuator 32 is secured to the actuator handle 30 and is used physically to engage and move the piston rod 24 along its longitudinal axis to dispense the fluid substance contained in the body 22 through a formed tip 34 in a controlled, variable amount during repetitive applications, the amount depending upon the skill and the desire of the user. The actuator 32 may be secured to the handle 30 by any suitable means. For example, one formed end 36 of the actuator 32 may be secured to a longitudinal end 38 of the handle 30 by being molded thereto or by being mechanically captured therein or by being affixed thereto by any suitable glue, adhesive or mechanical fastener. Transversely disposed at, for example, a 90° angle, to the formed end 36 of the actuator 32 is a second, formed elongate lever portion 40 for engagement along its length by a finger of a user. The junction 42 between the end 36 and the portion 40 of the actuator 32 may be viewed as an integrally formed hinge. The actuator 32 includes a third, inclined, gouge portion 44 having a sharpened or pointed tip 46 formed at its free end for engaging (FIGS. 4, 5 and 9) a central, solid portion 48 (FIG. 9) of the piston rod 24. The handle 30 includes an elongate slot 50 through which the portion 44 and the tip 46 extend to engage the portion 48 of the piston rod 24. The longitudinal dimension of the slot 50 may be varied, if desired, to limit the amount of the extension of the gouge portion 44 of the actuator 32 (FIG. 5). A junction 52 between the lever portion 40 and the gouge portion 44 of the actuator 32 may also be viewed as an integrally formed hinge.

Preferably, at least the body 22, containing a fluid substance such as the above-mentioned topical dental preventative medicine, is disposable after depletion. Therefore, it is desirable that at least the handle 30 be separable from the body 22 (FIG. 6) of the dispenser 20. If desired, the formed tip 34 may also be separable from the forward end of the disposable body 22, in which case, both the handle 30 and the tip 34 may be viewed as reusable components of the dispenser 20. The handle 30 and the tip 34 may be attached to the body 22 by any suitable means. For example, a first longitudinal end 54 (FIGS. 3 and 6) of the body 22 is formed with an annular groove or recess 56 for releaseably receiving and retaining therein an enlarged annular shoulder 58 formed at a second longitudinal end 60 of the handle 30. Due to the inherent resiliency of the moldable plastic material preferably used to form the body 22 and the handle 30 and the formed tip 34, a releaseable, snap fit is achieved between the shoulder 58 and the groove 56 to releaseably secure together the body 22 and the handle 30. Similarly, an annular groove or recess 62 may be formed at a longitudinal end 64 of the body 22 opposite to the end 54 for releaseably receiving an enlarged, annular mating shoulder 66 formed at a longitudinal end 68 of the formed tip 34. This snap fit between the shoulder 66 and the groove 62 effects the releaseable engagement between the body 22 and the formed tip 34.

Figures 1, 2:
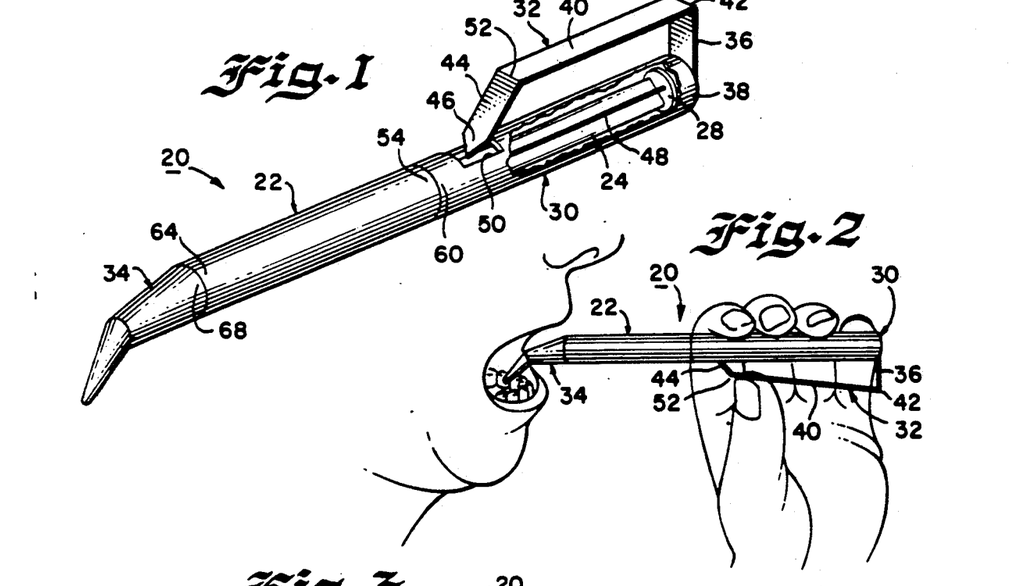
FIG. 1 is a perspective view of a dispenser, particularly adapted for use by a patient in applying topical dental medicine to himself, constructed in accordance with the principles of the present invention.
FIG. 2 is a perspective view of the dispenser of FIG. 1 illustrating the manner in which a topical dental medicine may be applied by a person to his own oral cavity.

As illustrated in FIG. 2, topical dental medicine may be applied by a patient using the dispenser 20 to his own oral cavity to prevent or treat periodontal disease, such as gingivitis. As illustrated, a bead of a topical dental medicine may be applied along the gumline of a patient's own jaw by grasping the actuator handle 30 in the patient's hand and by applying finger force to the lever portion 40 of the actuator 32 to drive the inclined gouge portion 44 into physical deforming contact with the piston rod 24 to move the piston 26 in a forward direction within the body 22. In the process, a bead of the topical dental medicine from the formed tip 34 is deposited along desired portions of the patient's gumline. As illustrated, preferably, the formed tip 34 is formed at an angle greater than 0° and less than 180° to the longitudinal axis of the body 22 to facilitate the dispensing of the topical dental medicine in the oral cavity of the user.

Figures 6, 7, 8, 9, 10:
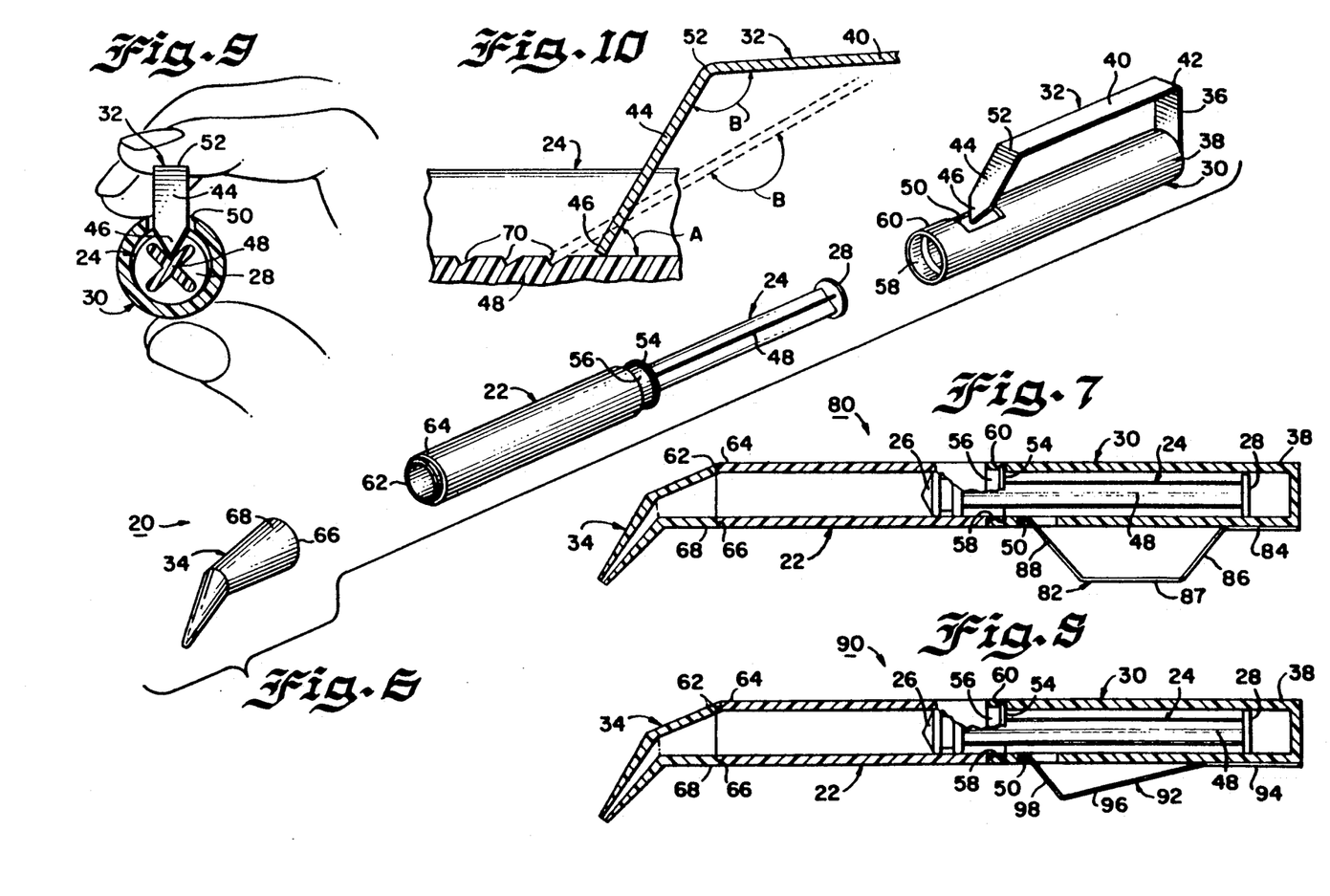
FIG. 6 is an exploded perspective view of the dispenser of FIG. 1.
FIGS. 7 and 8 are cross-sectional views, similar to the view of FIG. 3, depicting alternative configurations for the actuator of the dispenser.
FIG. 9 is an enlarged, partially perspective and partially cross-sectional view of the dispenser of FIG. 4 illustrating the actuator thereof in contact with the piston rod.
FIG. 10 is an enlarged, illustrative view of the manner in which gouges or teeth are formed by the actuator along the piston rod of the dispenser of FIGS. 1 and 9.

In accordance with an important feature of the present invention, forward movement of the piston rod 24 and of the piston 26 within the body 22 is achieved by the use of a gouge portion 44 formed from a material, i.e., metal, having a greater hardness than the material used to form the piston rod 24. For example, the actuator 32 may be formed from a suitable metal material, such as stainless steel type 302 having a hardness of approximately 40/45 as measured on the Rockwell C scale. Preferably, the piston rod 24 is formed from a suitable moldable, less hard, plastic material, for example, polyethylene having a hardness of approximately 50-70 as measured on the Shore D scale. As a result, as illustrated in FIGS. 9-10, the tip 46 of the gouge portion 44 of the actuator 32 physically deforms the surface of the piston rod 24 to form a series of gouges or teeth 70 along the length of the piston rod 24 during successive dispensing operations of the dispenser 20.

Figure 3:
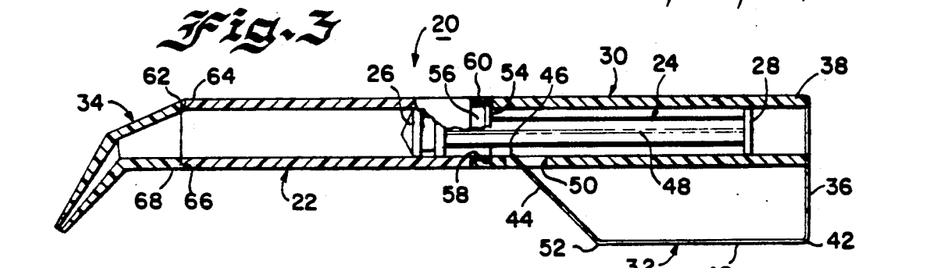
FIG. 3 is a cross-sectional view of the dispenser of FIG. 1 depicting the actuator and piston rod of the dispenser prior to engagement.

In order to achieve forward movement of the piston rod 24 and of the piston 26 within the body 22, an angle "A" between the inclined gouge portion 44, and more specifically the tip 46, and the outer surface of the piston rod 24 must be greater than 0° and less than 90°. In this manner, the gouge portion 44 is designed to contact, physically deform and move the piston rod in a forward direction. Importantly, the spacing between adjacent teeth 70, corresponding to the amount of fluid substance dispensed by the dispenser 20 during successive operations, may be varied, as desired, by a user by controlling the amount of finger force applied to the lever portion 40 of the actuator 32, thereby controlling the final angular disposition of or the amount of extension of the gouge portion 44 during a dispensing operation. More specifically, an angle "B" (FIG. 10), defining the junction 52, increases during the application of finger force to the lever portion 40. While the angle "B" between the lever portion 40 and the gouge portion 44 will not exceed 180° (the dotted line portion of FIG. 10), at which angle the gouge portion 44 is fully extended, a dispensing operation of the dispenser 20 may be terminated by an operator when the lever portion 40 and the gouge portion 44 are disposed at an angle "B" less than 180°, thereby limiting the amount of fluid substance dispensed during a particular operation of the dispenser 20. FIGS. 3, 4 and 5, respectively, depict the dispenser 20 prior to the initiation of a dispensing operation, at the beginning of a dispensing operation and at the end of a dispensing operation.

In this manner, an economical, simple and easy to use dispenser 20 is provided for use by a patient in dispensing fluid substances, for example, in applying a topical dental medicine to his own oral cavity, at a rate controlled by the skill and the desire of the patient.

The viscosity of the fluid substance to be dispensed by the dispenser 20 will influence the rate at which the dispenser 20 is capable of dispensing fluid substances. A very viscous fluid substance will exhibit a lag time that enables an experienced user to extrude a continuous bead of a fluid substance having a substantially constant cross-section at a rate corresponding to that at which the user moves the formed tip 34, in combination with the frequency and finger pressure applied to the actuator 32. Less viscous fluid substances can be delivered in discrete amounts controlled by both the frequency and finger pressure applied by the user and the geometry of the actuator 32. Therefore, for certain applications, it may be desirable to select a dispenser 20 having a different actuator configuration.

In accordance with an important feature of the present invention, alternative configurations for the actuator 32 are illustrated in FIGS. 7 and 8. More specifically, a dispenser 80 (FIG. 7) includes an actuator 82 having a first integrally formed end 84 secured to a body 22 by any suitable means, as discussed above. In addition, extending from the first formed end 84 is a second, inclined portion 86 adjacent to a third, elongate lever portion 87 that, in turn, is joined to a fourth, inclined gouge portion 88. Alternatively, a dispenser 90 (FIG. 8) includes an actuator 92 having a first integrally formed portion 94 for securing the actuator 92 to a body 22 by any suitable means, as discussed above. In addition, the actuator 92 includes a second, elongate, inclined lever portion 96 adjacent to and integrally formed with a third inclined gouge portion 98. The remaining components and the operation of the dispensers 80 and 90 are essentially the same as that discussed hereinabove with respect to the dispenser 20. The alternative configurations of the actuators 32, 82 and 92 may prove useful in selecting the most suitable one of the dispensers 20, 80 and 90 to deliver a particular fluid substance from a wide range of non-compressible fluid substances having different viscosities.

Figures 11, 12, 13:
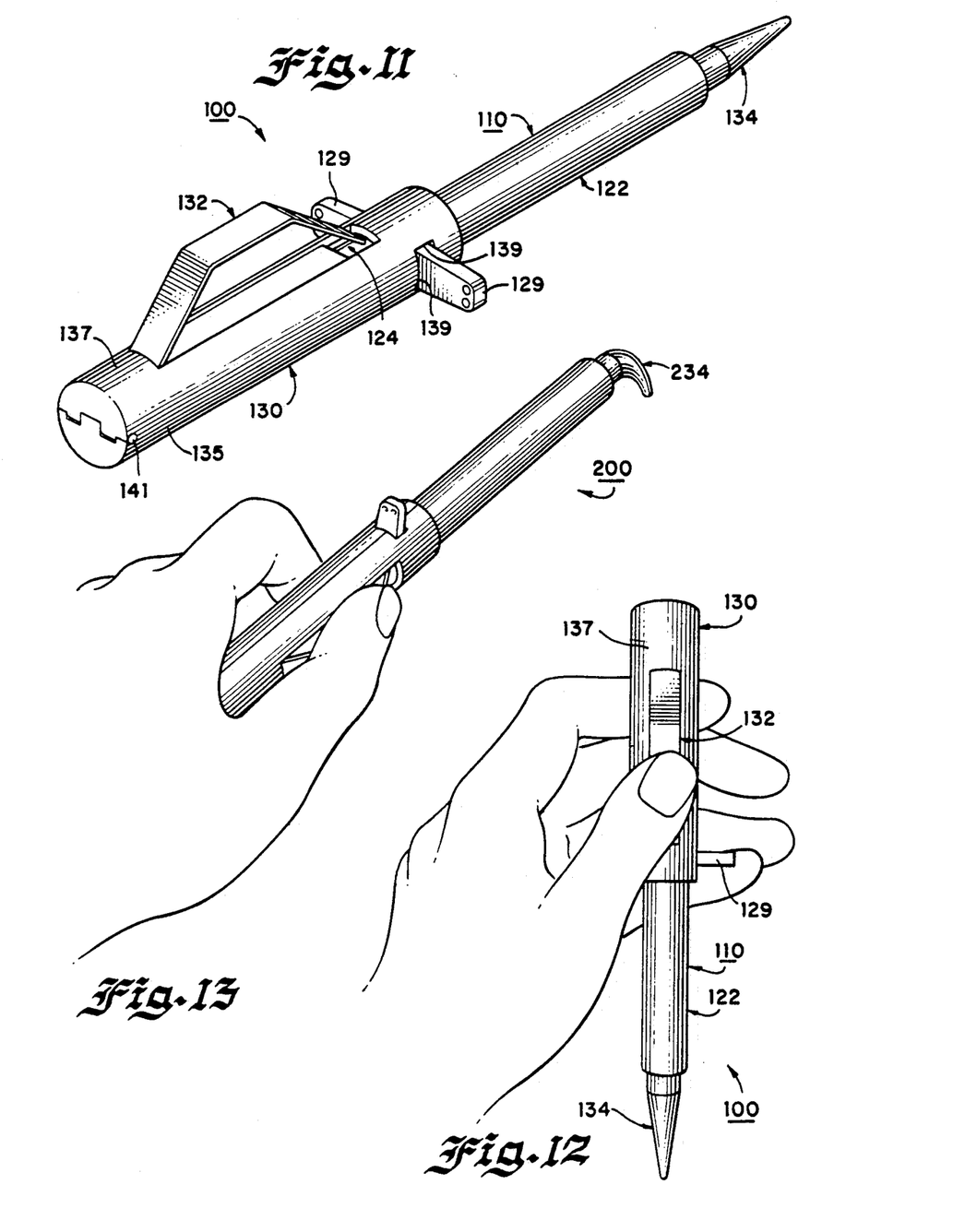
FIG. 11 is a perspective view of an alternative embodiment of a dispenser constructed in accordance with the principles of the present invention and having general applicability in dispensing any one of a number of different fluid substances.
FIG. 12 is a perspective view of the dispenser of FIG. 11 illustrating the manner in which the dispenser of FIG. 11 may be held by a user to dispense fluid substances.
FIG. 13 is a view similar to that of FIG. 12 depicting an alternative formed tip for dispensing fluid substances, such as cake frosting.
Figure 15:
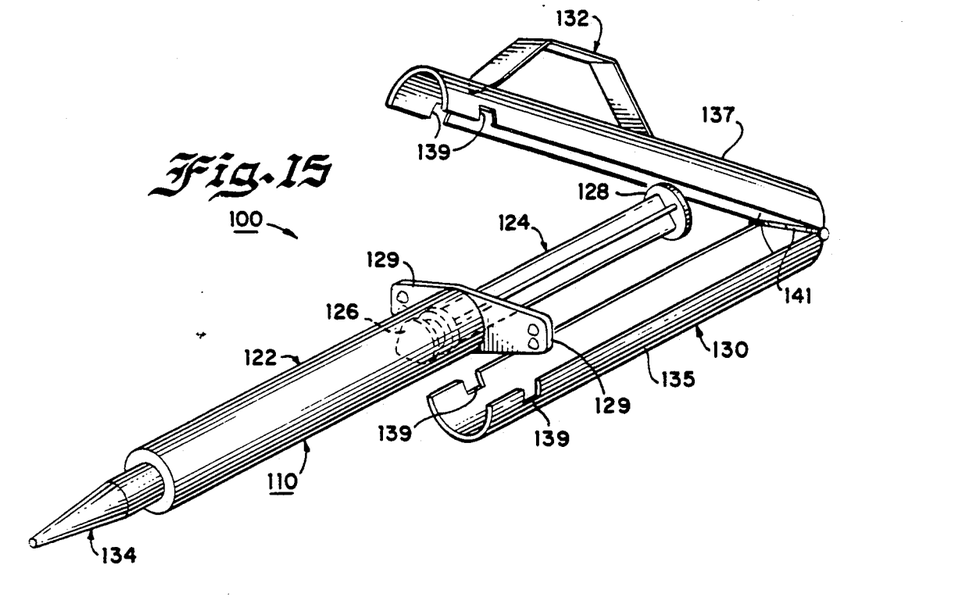
FIG. 15 is an exploded perspective view of the device of FIG. 11.

In accordance with a further important feature of the present invention and with reference to FIGS. 11, 12 and 15, a new and improved dispenser 100, constructed in accordance with the principles of the present invention, is illustrated for controllably dispensing a fluid substance. The dispenser 100 is of more general application than the dispenser 20 discussed above and is adapted to be used in dispensing fluid substances of many different types by means of the handheld, finger operated dispenser 100.

The dispenser 100 includes a conventional, disposable or replaceable piston-cylinder type syringe 110 having a generally cylindrical body 122, an elongate piston rod 124 and a formed tip 134. Unlike the formed tip 34 discussed hereinabove that is formed with a bend or an angle to facilitate the dispensing of a bead of topical dental medicine by a user in his own oral cavity, the formed tip 134 is formed without a bend for use in applications not requiring a bend. The formed tip 134 may, if desired, be formed in other configurations including, for particular applications, a bend or a reduced diameter dispensing tip such as a hollow needle tip. The syringe 110 also includes an enlarged piston 126 and a planar section or flange 128 disposed at opposite longitudinal ends of the piston rod 124. In addition, the syringe 110 includes a pair of oppositely extending ears or finger grips 129 formed integrally with the body 122 for facilitating the handling of the dispenser 110 by a user.

The dispenser 110 also includes a hinged, two-piece, actuator handle 130 to which is secured, by any suitable means as discussed above, a formed gouge or actuator 132. The actuator handle 130 is formed by two semi-cylindrical elongate body portions 135 and 137, each of which includes a pair of aligned, oppositely disposed recesses 139 for receiving portions of the finger grips 129. The body portions 135 and 137 are preferably joined together by a hinge 141 that permits the body portions 135 and 137 to be moved together to envelop the syringe 110 and to form the actuator handle 130 (FIG. 11). The body portions 135 and 137 can also be moved apart (FIG. 15) to permit the receipt of another syringe 110. Alternatively, the hinge 141 may be an integrally formed living hinge 141 formed during the molding process used to fabricate the body portions 135 and 137. The body portions 135 and 137 may be held together to form the actuator handle 130 (FIG. 11) by any suitable means. For example, the hinge 140 may include a spring to normally bias the body portions 135 and 137 to a closed position (FIG. 11). Except for its possible use in a wider range of applications and for the use of the hinged actuator handle 130, the components of the dispenser 120 are generally of the same nature and operate generally in the same manner as those described above with respect to the dispensers 20, 80 and 90.

The manner in which the dispenser 100 may be held by a user to dispense fluid substances, for example, at a location other than the oral cavity of the user, is illustrated in FIG. 12. Similarly, FIG. 13 illustrates the manner in which a dispenser 200, generally the same as the dispenser 100 discussed hereinabove except for the use of a formed tip 234 formed with a curve or a bend, may be used to apply a fluid substance, for example, cake frosting, to a surface in a desired pattern.

Figure 14A:
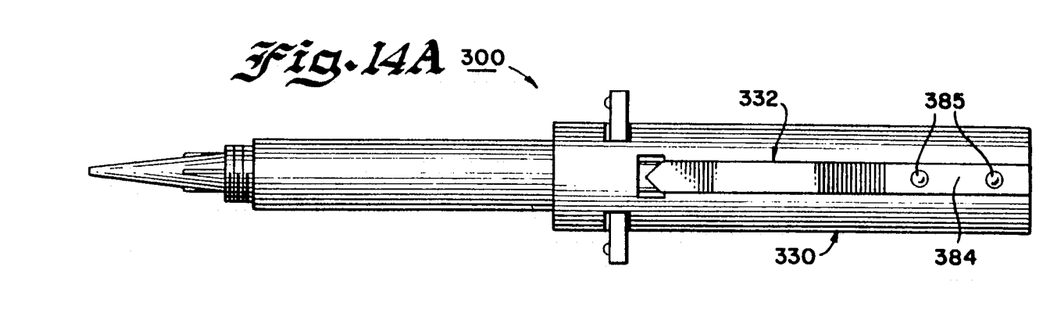
FIG. 14A is a view in elevation and FIGS. 14B and 14C are views in cross-section of an alternative embodiment of the dispenser of FIG. 11.
Figure 14B:
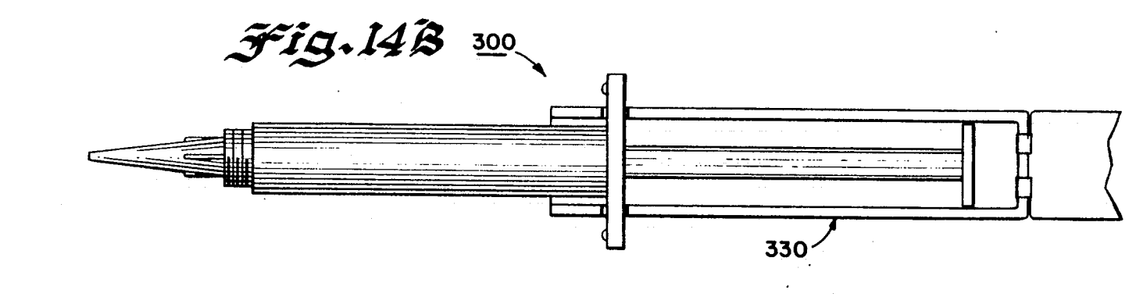
Figure 14C:
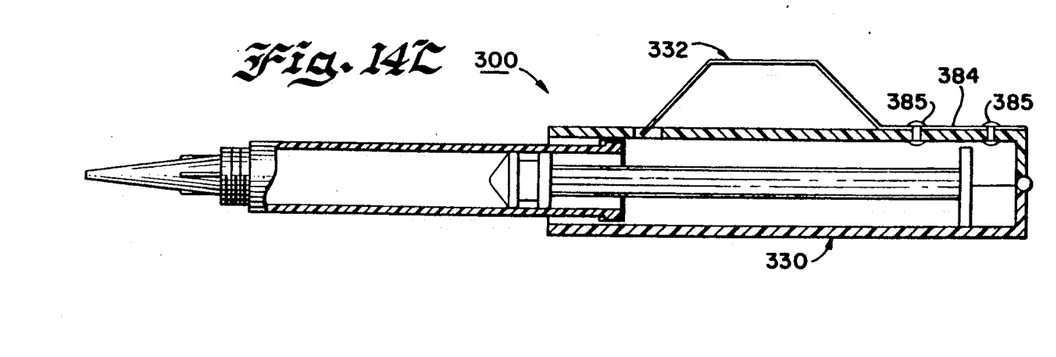

FIGS. 14A, 14B and 14C illustrate an alternative embodiment of a dispenser 300, constructed in accordance with the principles of the present invention, that includes a formed gouge or actuator 332 having a first integrally formed end 384 staked by a plurality of rivets 385 to an actuator handle 330. Other than the above differences, the components of the dispenser 300 are generally of the same nature and operate in the same manner as the corresponding components of the various dispensers 20, 80, 90, 100 and 200, discussed hereinabove.

Figure 16:
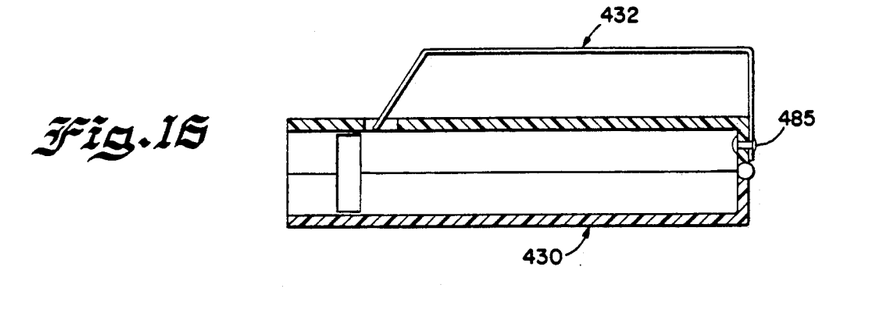
FIGS. 16 and 17 depict alternative embodiments of actuator handles for a dispenser constructed in accordance with the principles of the present invention.
Figure 17:
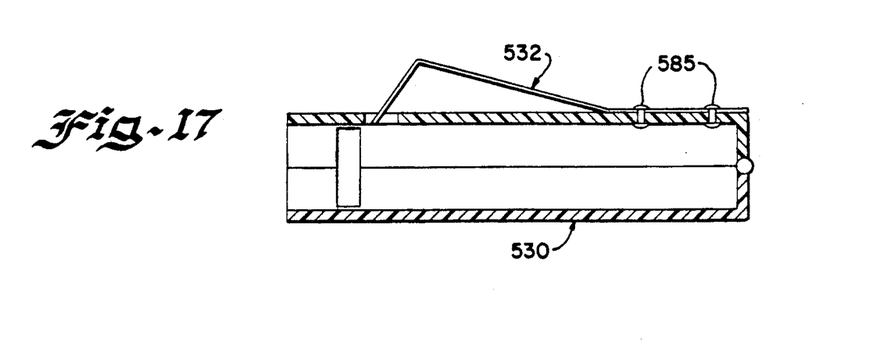

FIG. 16 illustrates an alternative embodiment of an actuator handle 430 and of a formed gouge or actuator 432 secured to the actuator handle 430 by a rivet 485 for use with the syringe 110 in generally the same manner as described hereinabove with respect to the dispenser 100. Similarly, FIG. 17 illustrates an alternative embodiment of a formed gouge or actuator 532 secured by a plurality of rivets 585 to an actuator handle 530 for use with a syringe 110 in generally the same manner as described hereinabove with respect to the dispenser 100.

Figures 18, 19:
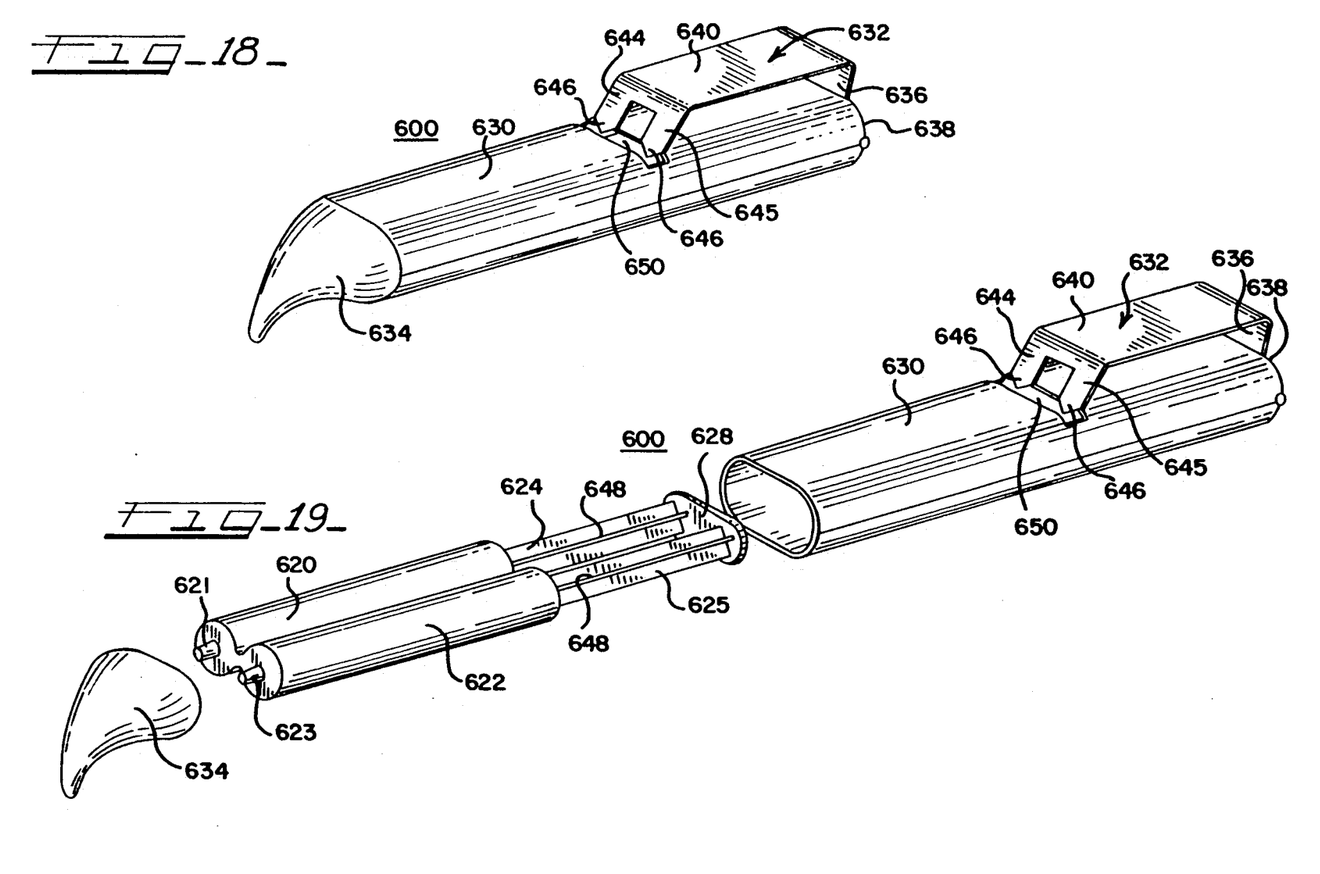
FIG. 18 is a perspective view of a further alternative embodiment of a dispenser constructed in accordance with the principles of the present invention.
FIG. 19 is an exploded perspective view of the dispenser of FIG. 18.

In accordance with the further important feature of the present invention, FIGS. 18 and 19 illustrate a further alternative embodiment of a new and improved dispenser 600, constructed in accordance with the principles of the present invention, for controllably dispensing a fluid substance. The dispenser 600 is particularly adapted for use by a patient in dispensing an extruded bead of a multiple component topical dental preventative medicine to selected sites within his own oral cavity by means of the hand-held, finger operated dispenser 600. The dispenser 600 includes a pair of elongate, integrally formed, generally cylindrical bodies 620 and 622, disposed parallel to each other, in which separate components of a fluid substance, such as a multiple component topical dental preventative medicine, to be dispensed by the dispenser 600 are disposed. Each of the bodies 620 and 622 is designed to hold one or more components of a fluid substance that are subsequently extruded through a nipple 621, associated with the body 620, and a nipple 623, associated with the body 622, for being mixed within and for being dispensed through a formed tip 634 of the dispenser 600. In this manner, one or more components of a fluid substance within the body 620 may be maintained separate from one or more other components of the fluid substance within the body 622 until such components are desired to be mixed and dispensed or applied through the formed tip 634. As depicted, the formed tip 634 is formed at an angle greater than 0° and less than 180° to the longitudinal axis of the bodies 620 and 622 to facilitate the dispensing of a fluid substance by the dispenser 600.

The dispenser 600 further includes a pair of elongate piston rods 624 and 625, respectively associated with the bodies 620 and 622, and each having a generally "X-shaped" transverse cross-section (FIG. 19) and an enlarged piston (not illustrated) disposed at one longitudinal end of each of the rods 624 and 625 for moving the components disposed within the bodies 620 and 622 therethrough and out of the nipples 621 and 623. The opposite longitudinal ends of the rods 624 and 625 are joined together by an enlarged planar section or flange 628 that ensures that the rods 624 and 625 are moved in unison through the bodies 620 and 622. Preferably, the outer dimensions of the flange 628 are configured to correspond to the inner dimensions of a complementarily shaped, elongate tubular actuator handle 630 to prevent substantial transverse shifting or lateral movement of the flange 628 within the handle 630. The body 630 may be formed as a one piece body or may be formed as a hinged two piece body generally of the type discussed hereinabove with respect to the body 130 (FIG. 15).

A formed, metal gouge or actuator 632 is secured to the handle 630 by any suitable means, as discussed hereinabove, and is used physically to engage and move the rods 624 and 625 along the longitudinal axes of the bodies 620 and 622 and of the handle 630. In this manner, the fluid substance contained within the bodies 620 and 622 is dispensed through the formed tip 634 in a controlled, variable amount during repetitive applications, the amount depending upon the skill and the desire of the user. A formed end 636 of the actuator 632 may be secured to a longitudinal end 638 of the handle 630 by being molded thereto or by being mechanically captured therein by being affixed thereto by any suitable glue, adhesive or mechanical fastener. Transversely disposed at, for example, a 90° angle to the formed end 636 of the actuator 632 is a second, formed elongate lever portion 640 for engagement along its length by a finger of a user. The actuator 632 includes a pair of integrally-formed, inclined, gouge portions 644 and 645 each having a sharpened or pointed tip 646 formed at their free ends for respectively engaging the central, solid portions 648 of the rods 624 and 625. The portions 644 and 645 are configured such that their angular disposition with respect to the portions 648 upon initial engagement therewith is at an angle greater than 0° and less than 90°. The handle 630 includes an elongate slot 650 through which the portions 644 and 645 and their associated tips 646 extend to engage the portions 648 of the rods 624 and 625.

The actuator 632 is designed and configured to move the rods 624 and 625 within the bodies 620 and 622 and within the handle 630 in generally the same manner as discussed hereinabove with respect to the embodiment of FIGS. 1 through 6. In contrast thereto, however, the two rods 624 and 625 are designed to be moved by the actuator 632 in unison in dispensing components of a fluid substance through the formed tip 634.

Figure 20:
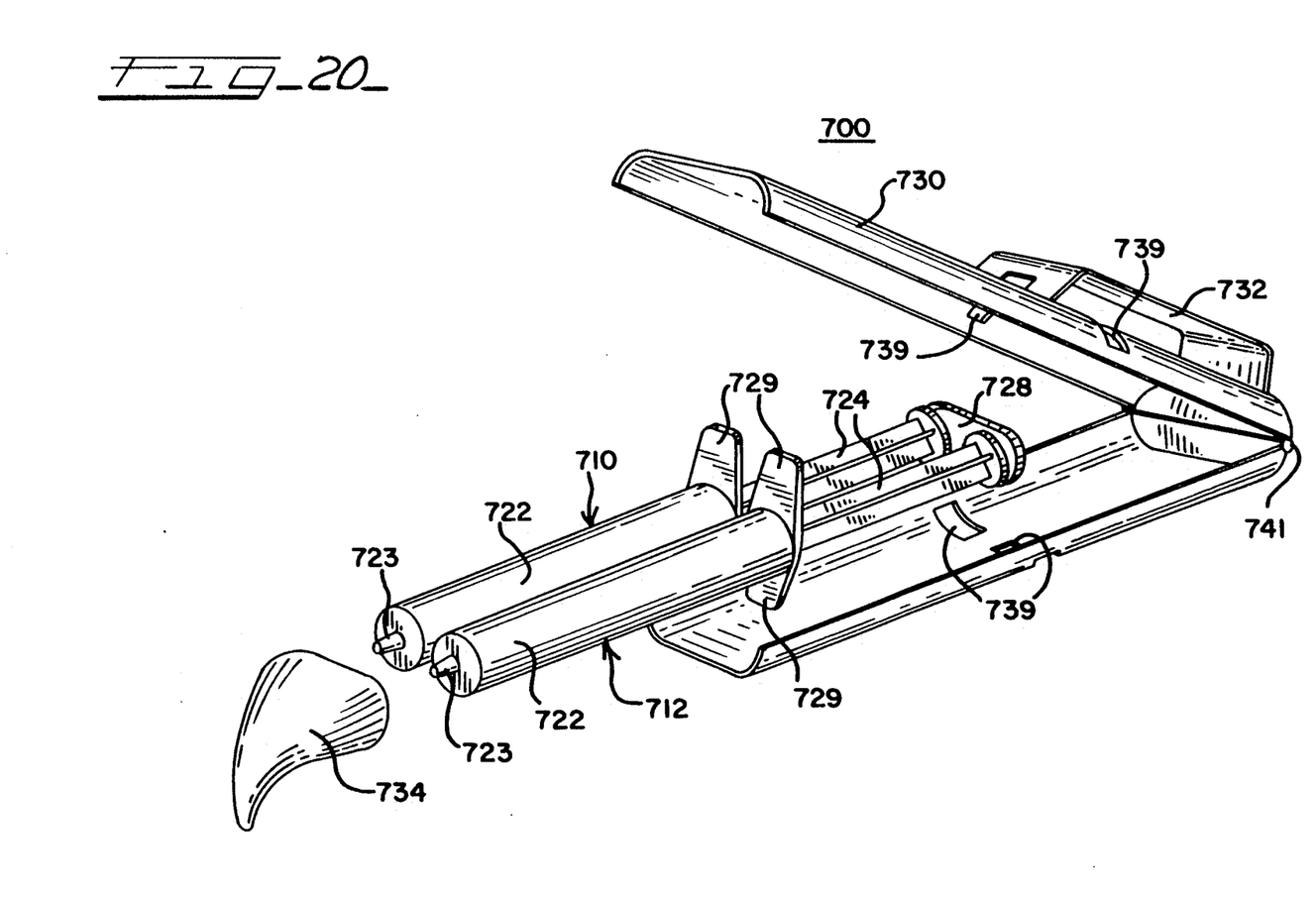
FIG. 20 is an exploded perspective view of a further alternative embodiment of a dispenser constructed in accordance with the principles of the present invention.

FIG. 20 illustrates a further alternative embodiment of a dispenser 700, constructed in accordance with the principles of the present invention, that is generally similar in theory and operation to the dispenser 600 (FIGS. 18 and 19) but utilizes a pair of conventional, disposable or replaceable piston-cylinder type syringes 710 and 712 disposed parallel to each other within a hinged actuator handle 730. Each of these syringes 710 and 712 includes an elongate, generally cylindrical body 722 and a nipple 723 disposed at one longitudinal end thereof. Components of a fluid substance contained within the bodies 722 may be mixed in and dispensed or applied through a formed tip 734, generally of the same construction as the formed tip 634.

Each of the syringes 710 and 712 also includes an elongate piston rod 724 and a pair of oppositely extending ears or finger grips 729 formed integrally with the bodies 722 for facilitating the handling of the dispenser 700 by a user. The rods 724 are joined together at their outward longitudinal ends by a planar section or flange 728. The hinged, actuator handle 730 includes a formed gouge or actuator 732, generally of the same construction as the actuator 632, and two pairs of aligned, oppositely disposed recesses 739 for receiving oppositely extending portions of the finger grips 729. The handle 730 includes a hinge 741 that generally is formed and functions in the same manner as the hinge 141 (FIG. 15), discussed hereinabove.

Obviously, many modifications and variations of the present invention are possible in light of the above teachings. Thus, it is to be understood that, in accordance with the appended claims, the invention may be practiced otherwise than as specifically described hereinabove.

What is claimed and desired to be secured by Letters Patent of the United States is:

1. A non-compressible fluid substance dispenser comprising an elongate body for containing an amount of a fluid substance to be dispensed by said dispenser, including a fluid dispensing aperture, means for ejecting a fluid substance from said fluid dispensing aperture, said ejecting means comprising a first elongate member having an outer surface of a first surface hardness, and means for actuating said ejecting means, said actuating means comprising a physically deformable elongate lever member having integral contacting means for engaging and physically deforming said outer surface to effect actuation of said ejecting means, said contacting means having a second surface hardness, said second surface hardness being greater than said first surface hardness to enable the physical deformation of said outer surface by said contacting means, such that force applied to the lever member reversibly physically deforms the lever member, causing the contacting means to contact, physically deform and firmly grip said first elongate member, and causing the contacting means to move toward said fluid dispensing aperture thereby causing said first elongate member to move toward said fluid dispensing aperture while maintaining a firm grip on the outer surface of said first elongate member.

2. A non-compressible fluid substance dispenser as recited in claim 1 wherein said body comprises an elongate generally cylindrical body.

3. A non-compressible fluid substance dispenser as recited in claim 2 wherein said first elongate member comprises a piston rod and wherein said ejecting means further comprises a piston secured to said piston rod at one longitudinal end thereof.

4. A non-compressible fluid substance dispenser as recited in claim 3 wherein said lever member comprises a formed metal handle portion extending outwardly from said body.

5. A non-compressible fluid substance dispenser as recited in claim 4 wherein said contacting means comprises an integral metal portion of said metal lever member, said integrally formed contacting means being angularly disposed with respect to said outer surface upon initial engagement therewith at an angle greater that 0° and less than 90°.

6. A non-compressible fluid substance dispenser as recited in claim 4 wherein said metal lever member is formed from stainless steel and wherein said piston rod is formed from polyethylene.

7. A non-compressible fluid substance dispenser as recited in claim 1 wherein the fluid dispensing aperture is defined by a formed tip physically disposed at one end of said body through which the fluid substance is ejected from said body.

8. A non-compressible fluid substance dispenser as recited in claim 7 wherein said formed tip is formed at an angle greater than 0° and less than 180° to the longitudinal axis of said body to facilitate the dispensing of a fluid substance by said dispenser.

9. A non-compressible fluid substance dispenser as recited in claim 7 further comprising means for releaseably securing said formed tip to one longitudinal end of said body.

10. A non-compressible fluid substance dispenser as recited in claim 1 further comprising an elongate handle physically disposed at one longitudinal end of said body, said actuating means being physically securedly affixed to said handle.

11. A non-compressible fluid substance dispenser as recited in claim 10 wherein said handle includes an elongate slot formed therein through which said contacting means extends from said lever member for engaging and physically deforming said outer surface of said first elongate member.

12. A non-compressible fluid substance dispenser as recited in claim 11 wherein said handle comprises a pair of elongate body portions connected together by a hinge to enable said body portions to separate upon removal of said elongate body from said dispenser.

13. A non-compressible fluid substance dispenser as recited in claim 10 wherein said elongate body and said ejecting means comprise a syringe for containing a non-compressible fluid substance.

14. A non-compressible fluid substance dispenser as recited in claim 10 wherein said first elongate member includes a flange transversely disposed with respect to the longitudinal axis of said first elongate member at one longitudinal end of said first elongate member, said elongate handle being generally cylindrical in shape and having an inner diameter, said flange being generally round in shape and having an outer diameter, said flange being movable within and along the longitudinal axis of said elongate handle and said outer diameter being slightly less than said inner diameter to enable the movement of said flange along the longitudinal axis of said handle and to prevent substantial movement of said flange within said handle in a direction transverse to the longitudinal axis of said handle.

15. A non-compressible fluid substance dispenser as recited in claim 10 further comprising means for releasably securely attaching said elongate handle at one longitudinal end of said elongate body, said first elongate member being disposed within said elongate handle and said lever member being disposed externally of said elongate handle.

16. A non-compressible fluid substance dispenser as recited in claim 1 further comprising a fluid substance disposed in said elongate body.

17. A non-compressible fluid substance dispenser as recited in claim 16 wherein said fluid substance comprises a topical dental medicine.

18. A non-compressible fluid substance dispenser as recited in claim 17 wherein said ejecting means and actuating means are configured to enable said dispenser to be held in the hand of a user and to enable said deformable lever member to be squeezed by at least one of the digits of the hand of the user to facilitate the self-application of said topical dental medicine by the user.

19. A non-compressible fluid substance dispenser as recited in claim 1 wherein the physical deformation of said first elongate member forms a series of teeth along said outer surface of said first elongate member by said contacting means during successive operations of said dispenser, the spacing between adjacent teeth being determined by the user of said dispenser during the operation of the dispenser by the user.

20. A method of applying a topical dental medicine to oneself comprising the steps of
holding a dispenser containing said topical dental medicine in one's own hand,
positioning a tip of said dispenser through which said topical dental medicine is extruded in one's own oral cavity,
pressing against a reversibly deformable level member to cause a contacting means portion of said lever member to contact an elongate movable member of said dispenser such that hand force applied to the lever member reversibly physically deforms the lever member, causing the contacting means to contact, physically deform by cutting its own notch and firmly grip said first elongate member, and causing the contacting means to move toward said fluid dispensing aperture thereby causing said first elongate member to move toward said fluid dispensing aperture while maintaining a firm grip on the outer surface of said first elongate member, the movement of said elongate movable member being in an amount determined by the amount of said topical dental medicine to be applied to oneself during a specific operation of said dispenser.

21. A method for applying a topical dental medicine to oneself as recited in claim 20 wherein said pressing step and said causing step are repeated by oneself to effect the application of said topical dental medicine to desired portions of the oral cavity of oneself.

22. A handheld finger operated fluid substance dispenser comprising
an elongate body for containing a fluid substance to be dispensed by said dispenser, a formed tip disposed at one longitudinal end of said elongate body through which said fluid substance is dispensed from said dispenser, a manually engageable handle disposed at the opposite longitudinal end of said body, means for ejecting a fluid substance from said body, said ejecting means being at least partially disposed within said handle and comprising an elongate piston rod having an outer surface of a first surface hardness, and means for moving said elongate piston rod along the longitudinal axis of said handle, said moving means comprising a formed actuator having a piston rod-contacting portion and having at least a reversibly physically deformable lever member portion thereof disposed externally of said handle, said piston rod-contacting portion being integral with the lever member such that physical deformation of the lever member reversibly physically changes the angular disposition of the contacting portion with respect to the piston rod, said lever member portion of said actuator being adapted to be manually engaged and depressed to effect contact with and the physical deformation of the outer surface of said piston rod by said piston rod-contacting portion of said actuator to thereby cut its own notches in the piston rod outer surface, thereby to effect the movement of said piston rod along the longitudinal axis of said handle and the resultant dispensing of said fluid substance from said body, the amount of said fluid substance dispensed during any single operation of said dispenser being dependent upon the extent of the depression of said actuator, the contacting portion of said actuator being angularly disposed with respect to said outer surface of said piston rod upon initial contact therewith at an angle greater than 0 and less than 90°.

23. A handheld finger operated fluid substance dispenser as recited in claim 22 wherein said body comprises an elongate generally cylindrical body.

24. A handheld finger operated fluid substance dispenser as recited in claim 23 wherein said ejecting means further comprises a piston secured to said piston rod at one longitudinal end thereof, said piston being disposed in said body for movement along the longitudinal axis of said body.

25. A handheld finger operated fluid substance dispenser as recited in claim 22 wherein said actuator is formed from metal and wherein said piston rod is formed from a moldable plastic material.

26. A handheld finger operated fluid substance dispenser as recited in claim 22 wherein said formed tip is formed at an angle greater than 0° and less than 180° to the longitudinal axis of said body to facilitate the dispensing of a fluid substance by said dispenser.

27. A handheld finger operated fluid substance dispenser as recited in claim 22 further comprising means for releaseably securing said formed tip to one longitudinal end of said body.

28. A handheld finger operated fluid substance dispenser as recited in claim 27 further comprising means for releaseably securely attaching said handle to the opposite longitudinal end of said body from said one longitudinal end.

29. A handheld finger operated fluid substance dispenser as recited in claim 22 wherein said handle includes an elongate slot formed therein through which said actuator extends to contact and physically deform said outer surface of said piston rod.

30. A handheld finger operated fluid substance dispenser as recited in claim 22 wherein said handle comprises a pair of elongate body portions and means for interconnecting said body portions, said body portions being movable with respect to each other to enable the removal of said elongate body from said handle.

31. A handheld finger operated fluid substance dispenser as recited in claim 22 further comprising a fluid substance disposed in said elongate body.

32. A handheld finger operated fluid substance dispenser as recited in claim 31 wherein said fluid substance comprises a topical dental medicine.

33. A handheld finger operated fluid substance dispenser as recited in claim 22 wherein the lever member portion is adapted to be manually engaged and depressed to effect contact with and physical deformation of the outer surface of said piston rod-contacting portion of said actuator, whereby a series of teeth are formed along said outer surface of said piston rod by said actuator during successive operations of said dispenser, whereby the spacing between adjacent teeth can be determined by the user of said dispenser during the operation of the dispenser by the user.

34. A handheld finger operated fluid substance dispenser comprising an elongate body for containing a fluid substance to be dispensed by said dispenser, a formed tip disposed at one longitudinal end of said elongate body through which said fluid substance is dispensed from said dispenser, a manually engageable elongate handle disposed at the opposite longitudinal end of said body, the longitudinal axis of said handle being generally parallel to the longitudinal axis of said body, means for ejecting a fluid substance from said body, said ejecting means being at least partially disposed within said handle and comprising an elongate piston rod having an outer surface, means for moving said elongate piston rod along the longitudinal axis of said handle, said moving means comprising a formed actuator having at least a reversibly physically deformable lever member portion thereof disposed externally of said handle and a piston rod-contacting portion, said piston rod-contacting portion being integral with the lever member such that physical deformation of the lever member reversibly physically changes the angular disposition of the contacting portion with respect to the piston rod, said lever member portion of said actuator being adapted to manually engage said outer surface of said piston rod to cut its own notch and thereby effect the movement of said piston rod along the longitudinal axis of said handle and the resultant dispensing of said fluid substance from said body, the amount of said fluid substance dispensed during any single operation of said dispenser being dependent upon the extent of the movement of said actuator by the user of said dispenser to enable variable amount of said fluid substance to be dispensed by said dispenser upon successive operations of said dispenser.

35. A handheld finger operated fluid substance dispenser as recited in claim 34 further comprising means formed along said outer surface of said piston rod for coacting with said actuator to effect the movement of said piston rod along the longitudinal axis of said handle and the resultant dispensing of said fluid substance from said body.

36. A handheld finger operated fluid substance dispenser as recited in claim 35 wherein said coacting means comprises a plurality of teeth formed along said outer surface of said piston rod.

37. A handheld finger operated fluid substance dispenser as recited in claim 34 wherein the contacting portion of said actuator is angularly disposed with respect to said outer surface of said piston rod upon initial contact therewith at an angle greater than 0° and less than 90°.

38. A handheld finger operated fluid substance dispenser as recited in claim 34 wherein said body comprises an elongate generally cylindrical body and wherein said ejecting means further comprises a piston secured to said piston rod at one longitudinal end thereof and disposed within said body.

39. A handheld finger operated fluid substance dispenser as recited in claim 34 wherein said actuator is formed from metal and wherein said piston rod is formed from a moldable plastic material.

40. A handheld finger operated fluid substance dispenser as recited in claim 34 wherein said formed tip is formed at an angle greater than 0° and less than 180° to the longitudinal axis of said body to facilitate the dispensing of a fluid substance by said dispenser.

41. A handheld finger operated fluid substance dispenser as recited in claim 34 further comprising means for releaseably securing said formed tip to said one longitudinal end of said body and means for releaseably securing said handle to said opposite longitudinal end of said body.

42. A handheld finger operated fluid substance dispenser as recited in claim 34 wherein said handle includes an elongate slot extending parallel to the longitudinal axis of said handle through which said actuator extends for contacting said outer surface of said piston rod.

43. A handheld finger operated fluid substance dispenser as recited in claim 34 wherein said handle comprises a pair of elongate body portions and means for interconnecting said elongate body portions and for enabling said body portions to move with respect to each other to effect the removal of said elongate body from said dispenser.

44. A handheld finger operated fluid substance dispenser as recited in claim 34 wherein said elongate body and said ejecting means comprise a syringe for containing a non-compressible fluid substance.

45. A handheld finger operated fluid substance dispenser as recited in claim 34 further comprising a fluid substance disposed in said elongate body.

46. A handheld finger operated fluid substance dispenser as recited in claim 45 wherein said fluid substance comprises a topical dental medicine.

47. A handheld finger operated fluid substance dispenser as recited in claim 46 wherein said formed tip and said handle and said ejecting means and said moving means are configured to enable said dispenser to be held in the hand of a user and to enable said actuator to be operated by at least one of the digits of the hand of the user to facilitate the self-application of said topical dental medicine to the oral cavity of the user.

48. A handheld finger operated fluid substance dispenser as recited in claim 47 wherein said topical dental medicine comprises a topical dental medicine for preventing the occurrence of gingivitis.

49. A non-compressible fluid substance dispenser comprising
a plurality of spaced apart, elongate body means for containing components of a fluid substance to be dispensed by said dispenser,
means for ejecting said components from said bodies, said ejecting means comprising a plurality of elongate first members, at least one of said first members being operatively associated with each of said bodies, each of said first members having an outer surface of a first surface hardness, and
means for actuating said ejecting means, said actuating means comprising a physically deformable elongate lever member having integral contacting means for engaging and physically deforming said outer surface to effect actuation of said ejecting means, said contacting means having a second surface hardness, said second surface hardness being greater than said first surface hardness to enable the physical deformation of said outer surface by said contacting means, such that hand force applied to the lever member reversibly physically deforms the lever member, causing the contacting means to contact, physically deform and firmly grip said first elongate member, and causing the contacting means to move toward said fluid dispensing aperture thereby causing said first elongate member to move toward said fluid dispensing aperture while maintaining a firm grip on the outer surface of said first elongate member.

50. A non-compressible fluid substance dispenser as recited in claim 49 wherein each of said bodies comprises an elongate generally cylindrical body.

51. A non-compressible fluid substance dispenser as recited in claim 50 wherein each of said first elongate members comprises a piston rod.

52. A non-compressible fluid substance dispenser as recited in claim 51 wherein said actuating means comprises a formed metal actuator, said physically deformable lever member comprising an integrally formed metal portion of said metal actuator.

53. A non-compressible fluid substance dispenser as recited in claim 52 wherein said contacting means comprises a tip of said metal portion of said metal actuator, said integrally formed metal portion being angularly disposed with respect to said outer surface upon initial engagement therewith at an angle greater than 0° and less than 90°.

54. A non-compressible fluid substance dispenser as recited in claim 49 further comprising a formed tip physically disposed at one end of said bodies through which a fluid substance is ejected from said dispenser.

55. A non-compressible fluid substance dispenser as recited in claim 54 wherein said formed tip is formed at an angle greater that 0° and less than 180° to the longitudinal axis of said bodies to facilitate the dispensing of a fluid substance by said dispenser.

56. A non-compressible fluid substance dispenser as recited in claim 49 further comprising an elongate handle physically disposed about said bodies, said actuating means being physically securely affixed to said handle.

57. A non-compressible fluid substance dispenser as recited in claim 56 wherein said handle includes elongate slot means formed therein through which said second elongate member extends for engaging and physically deforming said outer surface of said first elongate member.

58. A non-compressible fluid substance dispenser as recited in claim 57 wherein said handle comprises a pair of elongate body portions connected together by a hinge to enable said body portions to separate upon removal of said elongate bodies from said handle.

59. A non-compressible fluid substance dispenser as recited in claim 49 further comprising at least one component of a multiple component fluid substance disposed in each of said elongate bodies.

60. A non-compressible fluid substance dispenser as recited in claim 59 wherein said ejecting means and actuating means are configured to enable said dispenser to be held in the hand of a user and to enable said deformable lever member to be squeezed by at least one of the digits of the hand of the user to facilitate the self-application of said fluid substance by the user.

61. A non-compressible fluid substance dispenser as recited in claim 49 wherein the physical deformation of said first elongate member forms a series of teeth along said outer surface of each of said first members by said contacting means during successive operations of said dispenser, the spacing between adjacent teeth being determined by the user of said dispenser during the operation of the dispenser by the user.

62. A method of applying a topical dental medicine to oneself comprising the steps of
holding a dispenser containing said topical dental medicine in one'own hand,
positioning a tip of said dispenser through which said topical dental medicine is extruded in one's own oral cavity,
pressing against a reversibly deformable lever member to cause a contacting means portion of said lever member to contact a plurality of elongate movable members of said dispenser such that hand force applied to the lever member reversibly physically deforms the lever member, causing the contacting means to contact, physically deform to cut its own notch and firmly grip each of said elongate movable members, and causing the contacting means to move toward said fluid dispensing aperture thereby causing said elongate members to move toward said fluid dispensing aperture while maintaining a firm grip on the outer surface of said elongate members, the movement of said elongate movable members being in an amount determined by the amount of said topical dental medicine to be applied to oneself during a specific operation of said dispenser.

63. A method of applying a topical dental medicine to oneself as recited in claim 62 wherein said pressing step and said causing step are repeated by oneself to effect the application of said topical dental medicine to desired portions of the oral cavity of oneself.

64. A handheld finger operated fluid substance dispenser comprising
first and second elongate bodies for containing a fluid substance to be dispensed by said dispenser,
a formed tip disposed at one longitudinal end of said elongate bodies through which said fluid substance is dispensed from said dispenser,
a manually engageable handle disposed about at least a portion of said bodies,
means for ejecting a fluid substance from said bodies, said ejecting means being at least partially disposed within said handle and comprising first and second elongate piston rods respectively operatively associated with said first and second bodies and each having an outer surface of a first surface hardness, and
means for moving said elongate piston rods along the longitudinal axis of said handle, said moving means comprising a formed actuator having first and second contacting portions and having at least a reversibly physically deformable lever member portion thereof disposed externally of said handle, said piston rod-contacting portion being integral with the lever member such that physical deformation of the lever member reversibly physically changes the angular disposition of the contacting portion with respect to the piston rod,
said lever member portion of said actuator being adapted to be manually engaged and depressed to effect contact with and the physical deformation of the outer surfaces of said first and second piston rods respectively by said first and second piston rod-contacting portions of said actuator, thereby to effect the movement of said piston rods along the longitudinal axis of said handle and the resultant dispensing of said fluid substance from said bodies, the amount of said fluid substance dispensed during any single operation of said dispenser being dependent upon the extent of the depression of said actuator, the contacting portion of said actuator being angularly disposed with respect to said outer surfaces of said piston rod upon initial contact therewith at an angle greater than 0° and less than 90°.

65. A handheld finger operated fluid substance dispenser as recited in claim 64 wherein the physical deformation of said elongate members forms a series of teeth along said outer surfaces of said piston rods by said actuator during successive operations of said dispenser, the spacing between adjacent teeth being determined by the user of said dispenser during the operation of the dispenser by the user

* * * * *